United States Patent [19]

Geissen et al.

[11] Patent Number: 4,632,998

[45] Date of Patent: Dec. 30, 1986

[54] METHOD OF MIXING A FINELY DIVIDED LIQUID WITH A GAS TO PRODUCE A MIXTURE WITH THE LIQUID IN EXCESS OF ITS EXPLOSIVE LIMIT

[75] Inventors: Rolf Geissen, Mörfelden-Walldorf; Wolfgang Siebert, Frankfurt am Main, both of Fed. Rep. of Germany

[73] Assignee: Metallgesellschaft AG, Frankfurt am Main, Fed. Rep. of Germany

[21] Appl. No.: 657,331

[22] Filed: Oct. 3, 1984

[30] Foreign Application Priority Data

Oct. 4, 1983 [DE] Fed. Rep. of Germany ....... 3336022

[51] Int. Cl.$^4$ ............................................. C07D 307/89
[52] U.S. Cl. ..................................... 549/248; 549/249
[58] Field of Search ................................ 549/248, 249

[56] References Cited

U.S. PATENT DOCUMENTS

| | | | |
|---|---|---|---|
| 2,102,863 | 12/1937 | Talbert et al. | 549/248 |
| 3,480,565 | 11/1969 | Adams | 549/248 X |
| 3,518,284 | 6/1970 | Foster | 549/248 |
| 4,261,899 | 4/1981 | Gelbein | 549/249 |
| 4,369,327 | 1/1983 | Stockburger et al. | 549/248 |

FOREIGN PATENT DOCUMENTS 923041 4/1963 United Kingdom .

*Primary Examiner*—Richard L. Raymond
*Attorney, Agent, or Firm*—Karl F. Ross; Herbert Dubno

[57] ABSTRACT

A mixture will involve a risk of explosion if a concentration limit is exceeded. For this reason only part of the liquid is admixed to the gas in a first mixing zone so that the concentration limit above which there is a risk of explosion will not be exceeded. In a second mixing zone, the remaining quantity of liquid is added to the mixture withdrawn from the first mixing zone and the explosive concentration is exceeded. That mixture, in which the gas and liquid are distributed as homogeneously as possible, is reacted in a reaction zone. The reaction zone directly succeeds the second mixing zone.

4 Claims, 1 Drawing Figure

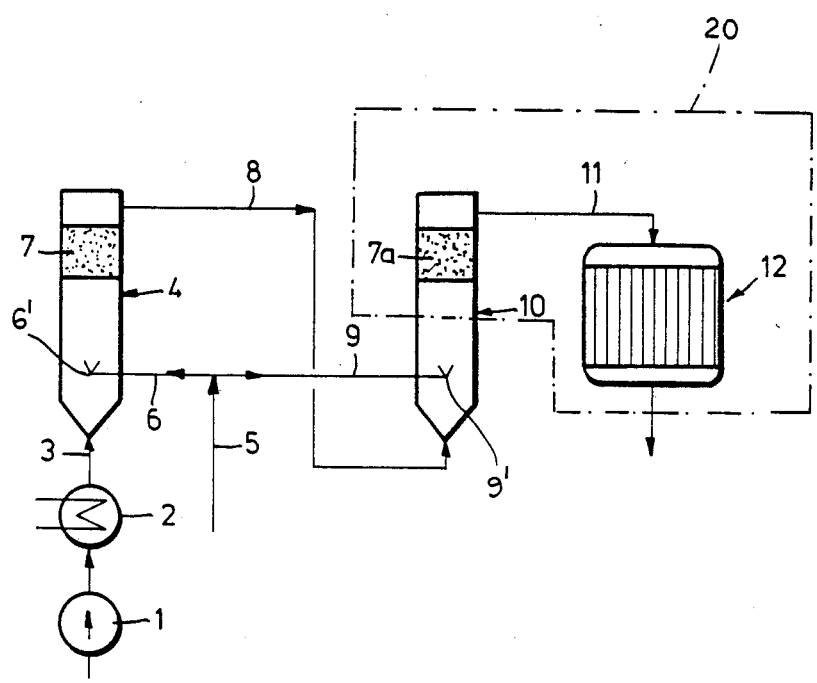

METHOD OF MIXING A FINELY DIVIDED LIQUID WITH A GAS TO PRODUCE A MIXTURE WITH THE LIQUID IN EXCESS OF ITS EXPLOSIVE LIMIT

FIELD OF THE INVENTION

Our present invention relates to a method of mixing a finely divided liquid with a gas to produce a mixture which will be explosive because the concentration of the liquid exceeds a certain limit (explosive concentration or limit), whereafter the mixture is reacted in a reaction zone. The liquid is finely divided, e.g. is in the form of a mist, aerosol or vapor as produced upon spraying by a nozzle or evaporation.

BACKGROUND OF THE INVENTION

For many reactions it is desirable to supply the starting components to the reaction zone in a distribution which is as uniform as possible, particularly if the reaction is to be effected in the presence of a catalyst. For this reason the previous practice has been to mix the starting components at a considerable distance from the reaction zone so that the desired homogeneity of the mixture is ensured by the mixing means and by an adequate residence time in the path leading to the reactor.

For certain reactions, such as the oxidation of orthoxylene or naphthalene with air to form phthalic anhydride, a large quantity of energy is usually required to pressurize the mixture to the pressure required in the reaction zone. For this reason it is desirable to increase the loading of the gas with the finely divided liquid so that the overall energy balance of the process will be improved. But a uniform distribution of the liquid in the gas cannot easily be achieved.

OBJECT OF THE INVENTION

The object of the invention is to provide a process which will ensure a uniform distribution of highly divided liquid in a gas with which it is reactive and to permit design of the apparatus using the process so that any explosion-preventing means are required only in the small part of the equipment.

SUMMARY OF THE INVENTION

In accordance with the invention this is accomplished in that such a partial quantity of the total liquid to be used is admixed to the gas in a first mixing zone so that an explosive concentration is not reached, while in a second mixing zone directly preceding the reaction zone the remaining quantity of the liquid is admixed to the mixture withdrawn from the first mixing zone, whereby the explosive concentration or limit of the liquid in the mixture is exceeded. In that process the equipment volume in which explosion-preventing means are required is restricted to the short line between the second mixing zone and the reaction zone.

A major part of the total quantity of liquid to be admixed to the gas is suitably supplied to the first mixing zone (preferably more than 95% of the explosive limit concentration) whereas the smaller remaining quantity of the liquid is supplied to the second mixing zone.

Reactions of the kind described hereinbefore which involve an explosion risk are mainly oxidation reactions with a gas which contains oxygen. For instance, when orthoxylene is to be reacted with air to effect a catalytic production of phthalic anhydride in the reaction zone, the explosive concentration of orthoxylene will be about 47 grams orthoxylene per cubic meter (STP) of air. For the sake of economy it is desired, however, to supply the reaction zone with a mixture containing per cubic meter (STP) of air at least 50 grams orthoxylene or more and, if possible, at least 60 grams orthoxylene. In that case the mixture withdrawn from the first mixing zone will contain about 45 grams orthoxylene, at most, per cubic meter (STP) of air. The explosion limit for a mixture of naphthalene and air is at about 45 grams naphthalene per cubic meter (STP) of air. The balance of the orthoxylene or naphthalene is added in the second mixer.

BRIEF DESCRIPTION OF THE DRAWING

The above and other objects, features and advantages will become more readily apparent from the following description, reference being made to the accompanying drawings, the sole FIGURE of which is a flow diagram illustrating the process of the invention.

SPECIFIC DESCRIPTION

The drawing shows a blower feeding gas to a heat exchanger 2 and then to a mixing zone. A pressurized-liquid line 5 feeds a part of the liquid required to react with the gas to a branch 6 having an atomizer 6' discharging the liquid in finely divided form into the mixing zone 4 to disperse the liquid in the gas at a liquid concentration below the explosive limit.

From the zone the liquid-in-gas suspension or vapor/gas mixture passes via line 8 to a second mixing zone 10 where the balance of the liquid is introduced via an atomizing nozzle 9' to a concentration exceeding the explosive limit.

The latter mixture then is fed to the reactor 12.

Only the portion of the apparatus enclosed in dot-dash lines 20 need be provided with explosion protection.

Air is displaced by the blower 1 and is heated in the heat exchanger 2 to a temperature of about 180° C. before it is supplied through line 3 to the first mixing zone 4. A major part of the orthoxylene conducted in the line 5 is supplied through a branch line 6 to the mixing zone 4 and is atomized therein.

The resulting mixture of liquid and gas is still inhomogeneous and flows through a turbulence-creating layer 7, which consists of packing elements or, e.g. expanded metal. A mixture containing 45 grams orthoxylene per cubic meter (STP) of air is withdrawn from the first zone 4 through line 8 and supplied to the second mixing zone 10.

The line 8 must have an adequate length of several meters because a homogeneous distribution of the liquid in the gas is achieved only during the flow through that line.

The smaller remaining quantity of the orthoxylene is supplied through the branch line 9 to the second mixing zone and is also atomized therein. Just as the first mixing zone, the second mixing zone contains a turbulence-creating layer 7a. The resulting homogeneous mixture has a concentration in excess of the explosion limit and flows through line 11 into the reactor 12, in which phthalic anhydride is produced.

If naphthalene rather than orthoxylene is used in the same process and for producing the same end product, the mixing zone 4 is supplied with evaporated naphthalene through lines 5 and 6 and with air through line 3 so that a mixture containing 43 to 44 grams naphthalene per cubic meter (STP) is obtained. Additional evaporated naphthalene is supplied to the mixture through line 9.

The explosion-preventing means are preferably mounted in the upper portions of the mixing zone 10 and of the reactor 12. Such means may consist, e.g. of rupture discs or long columns. For a reaction of naphthalene or orthoxylene with air, the reactor 12 contains a known fixed-bed catalyst, which consists mainly of $V_2O_5$ and is contained in tubes. The temperature in the reactor is about 360° to 400° C. and the heat produced by the exothermic reaction is indirectly dissipated by a molten salt bath.

We claim:

1. In a process for reacting a reaction mixture of a finely divided liquid selected from the group which consists of orthoxylene and naphthalene and air in a catalyst-containing reaction zone containing a catalyst and under conditions such that phthalic anhydride is produced as a reaction product and wherein the mixture of said liquid and air is at least at the explosive limit concentration of the liquid in the mixture, the improvement which comprises the steps of:
   (a) in a first mixing zone spaced from said reaction zone and free from catalyst, mixing a first portion of said finely divided liquid and air to produce a first mixture having a concentration of said liquid in said first mixture which is close to but below said explosive limit concentration;
   (b) feeding said first mixture into a second mixing zone free from catalyst and located between said first mixing zone and said catalyst-containing reaction zone and directly preceding said reaction zone in a flow direction of the mixture, and mixing said first mixture with a second portion of said finely divided liquid in said second mixing zone to produce said reaction mixture and with a concentration of said liquid in said reaction mixture exceeding the explosive limit concentration; and
   (c) directly feeding the reaction mixture upon its formation in said second mixing zone, directly preceding said reaction zone, into said reaction zone for contact with catalyst therein to produce phthalic anhydride.

2. The improvement defined in claim 1 wherein the reaction mixture from said second mixing zone fed into said reaction zone contains at least 50 grams of orthoxylene or naphthalene per cubic meter (STP) of air.

3. The improvement defined in claim 2 wherein the mixture produced in the first mixing zone is not less than 95% of the liquid required for said explosive limit concentration but is not more than 45 grams of orthoxylene and not more than 44 grams of naphthalene per cubic meter (STP) of air.

4. The improvement defined in claim 3 wherein the amount of liquid added in said second zone is sufficient to raise the concentration of liquid in the reaction mixture to at least 5% above that required for said explosive limit concentration.

* * * * *